(12) United States Patent
Tryggvason et al.

(10) Patent No.: US 6,689,090 B1
(45) Date of Patent: Feb. 10, 2004

(54) PERFUSION APPARATUS AND METHODS FOR PHARMACEUTICAL DELIVERY

(75) Inventors: Karl Tryggvason, Oulu (FI); Olavi Lukkarinen, Oulu (FI); Pirkko Heikkilä, Oulu (FI); Tarja Parpala, Oulu (FI)

(73) Assignee: Biostratum, Inc., Durham, NC (US)

( * ) Notice: Subject to any disclaimer, the term of this patent is extended or adjusted under 35 U.S.C. 154(b) by 575 days.

(21) Appl. No.: 09/167,894

(22) Filed: Oct. 7, 1998

Related U.S. Application Data

(63) Continuation of application No. 08/761,793, filed on Dec. 6, 1996, now Pat. No. 5,871,464, which is a continuation of application No. 08/442,189, filed on May 16, 1995, now abandoned.

(51) Int. Cl.[7] ................................................ A61M 3/00
(52) U.S. Cl. ............................................. 604/45; 604/43
(58) Field of Search .............................. 604/43, 45, 93, 604/131, 151, 506; 435/284.1, 286.5, 286.6

(56) References Cited

U.S. PATENT DOCUMENTS 5,494,822 A * 2/1996 Sadri ........................ 435/284.1

FOREIGN PATENT DOCUMENTS

WO          WO 93/09239          * 5/1993          .......... A61K/48/00

* cited by examiner

Primary Examiner—Manuel Mendez
(74) Attorney, Agent, or Firm—Fay, Sharpe, Fagan, Minnich & McKee, LLP

(57) ABSTRACT

The instant invention provides for apparatus and methods for the efficient administration of pharmaceuticals to target cells, tissues and/or organs, for a variety of functional uses.

1 Claim, 4 Drawing Sheets

PERFUSION APPARATUS AND METHODS FOR PHARMACEUTICAL DELIVERY

This application is a continuation of Ser. No. 08/761,793 filed Dec. 6, 1996 now U.S. Pat. No. 5,871,464, which is a continuation of Ser. No. 08/442,189 filed May 16, 1995 now abandoned.

FIELD OF THE INVENTION

The present invention relates to methods and apparatus for delivery of pharmaceuticals to target tissues in situ, in vivo, ex vivo, or in vitro.

BACKGROUND OF THE INVENTION

Advances in recombinant-DNA technology have made introduction of therapeutic genes into somatic cells possible (Anderson W F, Human gene Therapy. *Science* 256:808–813, 1992; Miller A D, Human gene therapy comes of age. *Nature* 357:455–457, 1992). In recent years several clinical trials involving human gene therapy have been accepted by regulatory agencies. The first of the approved clinical trials which have initiated human gene therapy aim at treating both inherited diseases (such as severe combined immunodeficiency caused by lack of adenosine deaminase in peripherial T-lymphoctes, cystic fibrosis, and familial hypercholesterolemia) as well as noninherited disease such as cancer (Wolfe J H, Recent progress in gene therapy for inherited disease. *Curr. Opinion in Pediatr.* 6: 213–219, 1994; Sanda M G et al., Gene therapy for urologic cancer. *J. Urology* 44:617–624, 1994; O'Malley B W et al., Somatic gene therapy in otolaryngology-head and neck surgery. *Arch. Otolaryngol. Head Neck Surgery* 119:1191–1197, 1993; Engelhardt J F et al., Direct gene transfer of human CFTR into human bronchial epithelia of xenografts with Ei-deleted adenoviruses. *Nature Genetics* 4: 27–34, 1993; Lemarchand P et al., Adenovirus-mediated transfer of recombinant human alpha1-antitrypsin cDNA to human endothelial cells. *PNAS (USA)* 89: 6482–6486, 1992; Jaffe H A et al., Adenovirus-mediated in vivo gene transfer and expression in normal rat liver. *Nature Genetics* 1:372–378, 1992).

The development of suitable, safe and effective gene transfer systems is a major goal of research in gene therapy. Thus far, viruses have been extensively used as vectors for gene therapy. For example, retroviruses have been widely used, but a major disadvantage is that they can only be used as vectors which target actively dividing cells. In addition, retroviruses do not accomodate large DNA inserts readily. Adeno-associated viruses are also limited in the ability to accomodate large inserts, yet replication defective adenovirus has been successfully used for transfer of a variety of genes into cells in culture and in vivo. Adenoviruses can accomodate larger inserts than retroviruses, but extrachromasomal expression usually only lasts for a few weeks. Herpes viruses have been exploited for specific gene transfer trials into the central nervous system. Herpes viruses can carry large foreign DNA inserts, and may remain latent for long periods of time. In spite of the availability of replication defective viruses, concerns about the safety and efficiency of such viral vectors has generated interest in the development of nonviral gene transfer systems such as liposome-DNA complexes and receptor mediated endocytosis (Felgner P L et al., *PNAS (USA)* 84: 7413–7417, 1987; Hyde *Nature* 362: 250–255, 1993; Nu G Y *J. Biol. Chem.* 266: 14338, 1991).

A major hurdle for effective gene therapy is the development of methods for targeting the gene transfer to appropriate target cells and tissues. Ex vivo gene transfer into explanted cultured cells and implantation of the treated cells has been used for the treatment of hematopoietic tissues (U.S. Pat. No. 5,399,346, issued Mar. 21, 1995, Anderson et al., hereby incorporated by reference). Direct injection into tissues, intravenous or intra-arterial administration, inhalation, or topical application have also been used. Major drawbacks to all of these methods are that the transduction is not highly selective, significant amounts of the therapeutic gene containing vector may be needed, and efficiency of the gene transfer is severely limited by the constraints of vector concentration, time of exposure to the target, and effectiveness of the gene transfer vector.

One area of active research has been gene therapy into mammalian kidneys, but the results have been disappointing because of problems with efficiency of gene transfer (Woolf A S et al., Gene transfer into the mammalian kidney: First steps towards renal gene therapy. *Kidney Int.* 43: Suppl. 39: S116–S119, 1993). Moullier et al. (Adenoviral-mediated gene transfer to renal tubular cells in vivo. *Kidney Int.* 45: 1220–1225, 1994), showed some adenovirus-mediated transfer of lacZ gene into rat tubular but not glomerular cells following a combination of infusion of the virus into the renal artery and retrograde infusion into the vector. Simple infusion of soluble virus does not appear to be an efficient transfer system. Better results were obtained by Tomita et al., (Direct in vivo gene introduction into rat kidney. *Biochem. Biophys. Res. Commun.* 186: 129–134, 1992), who infused a complex of Sendai virus and liposomes into the rat renal artery in vivo. This resulted in expression of the marker gene in about 15% of the glomerular cells.

It would be useful to the medical arts, to be able to have apparatus and methods for the efficient administration of gene therapy to target cells and tissues which overcomes the limitations inherent to each gene transfer vector.

SUMMARY OF THE INVENTION

In accordance with an aspect of the present invention, there is provided methods for the administration of pharmaceuticals to targets for functional use. (The term "pharmaceutical," as used herein, includes chemical drugs, protein drugs, nucleic acid drugs, combination chemical/protein/nucelic acid drugs, and gene therapy vectors. The term "functional use," as used herein, includes therapeutic treatment, prophylaxis, and/or production of recombinant proteins in vivo. The term "functional use" also includes the disruption of endogenous gene expression including the use of antisense, triplex forming, catalytic and otherwise disruptive pharmaceuticals. The term "functional use" also includes the expression of recombinant proteins in target tissues, whether of endogenous or exogenous origin. The term "target," as used herein, includes cells, tissues and/or organs. The term "gene therapy vector" is meant to include nucleic acid constructs which are single, double or triplex stranded, linear or circular, that are expressible or non-expressible constructs which can either encode for and express a functional protein, or fragment thereof, or interfere with the normal expression of a target gene, gene transfer and/or expression vectors.)

The administration of pharmaceuticals may take place where the target is in situ in a living subject. The administration may also take place wherein the target is first removed from a subject, manipulated ex vivo, and returned to the original or alternatively a second recipeint subject. In a preferred embodiment, the target is situated such that the circulation of the blood supply into and out of the target is relatively isolated. In a most preferred embodiment, the blood circulation into and out of the target is mostly via a single, or readily identified entering arteries and exiting veins. There are of course certain amounts of limited leakage due to small blood and lymphatic vessels.

The methods of the instant invention allow for a prolonged period of adminstration of pharmaceuticals to a target by way of recirculating a pharmaceutical containing solution through the target such that a perfusion effect occurs. The methods of the instant invention allow for prolonged administration because of the unique use of the perfusion method and the oxygenation of the pharmaceutical containing solution. In one embodiment, the perfusion apparatus and target forms a closed system whereby the pharmaceuticals are administered at a starting concentration and not adjusted during the time course of treatment. In another embodiment the pharmaceutical concentration is periodically adjusted so as to maintain or otherwise alter the concentration of pharmaceutical in the solution, or additional pharmaceuticals are added. In a preferred embodiment, the solution does not require replenishment during the course of treatment. In another embodiment, the solution volume can be replenished as leakage or other forms of loss occurs during the course of treatment. (The term "solution," as used herein refers to the medium in which the pharmaceutical is suspended, dissolved or otherwise maintained for delivery to the target, aka, the perfusate, and includes blood, serum, plasma, saline, and/or buffered solutions.) In a preferred embodiment, 350 ml of perfusate contains red blood cells (around 17% of hemocrit value), and can include about 25,000 IU heparin, about 20,000 IU penicillin and about 20,000 μg streptomycin in Krebs-Ringer solution in addition to the pharmaceutical.

The instant invention also provides for a perfusion apparatus comprising functionally connected by a perfusate transfer system, (a) a reservoir for perfusate, (b) means for propelling the perfusate through the apparatus, (c) means for oxygenation of the perfusate, (d) means for connecting the apparatus to and from the target.

The reservoir for the perfusate can be any container which can be sterilized and used to collect perfusate from the target. The reservoir is connected to the means for transporting the perfusate through the system by means of tubing. While perfusion may occur at room temperature of 20 C. in a preferred embodiment, the perfusion occurs a 37 C. Thus, in practice, the perfusate reservoir can be maintained at any desired temperature via, for example, a water bath.

In an embodiment where the means for propelling the perfusate is a peristaltic pump, the tubing is preferrably silicone or other such suitable pliable tubing. Where the means for propelling the perfusate is a peristaltic pump, no contact is made between the perfusate and any part of the pump directly. In the case where a pump with, for example an impeller blade is used, then the perfusate comes into direct contact with a part of the pump. In the usual configuration using a peristaltic pump, the tubing from the reservoir passes through the pump and connects with the means for oxygenating the perfusate.

The means for oxygenating the perfusate can be any form of artificial lung, or aeration device such that the perfusate is oxygenated with out over agitation and susequent frothing. In one embodiment the means for oxygenating the perfusate is a membrane lung which consists of a length of semi-permeable tubing packed into a gas chamber into which is circulated oxygen rich gas for oxygenating the perfusate as it pass through the length of tubing. In a preferred embodiment, the membrane lung contains about 8 m of silicon tubing of approximately 1.47 mm inside diameter, and the gas circulated in the chamber is carbogen gas (comprised of 95% oxygen, 5% carbon dioxide).

In general, the target is cannulated and connected to tubing connecting from the means for oxygenating the perfusate, and leading to the perfusate reservoir. In one configuration, the perfusate is pumped from a reservoir, through a means for oxygenating the perfusate, into the target, through the target, and back into the reservoir. The location of the pumping means in relation to the other components can be varied. The number of each component can also be varied.

Thus the instant invention provides for a method of administering a pharmaceutical to a target whereby the target is mostly isolated and continuosly perfused with a perfusate containing the pharmaceutical, and said perfusate is recirculated and oxygenated. The instant invention provides for an apparatus for the administration of pharmaceuticals to a target comprising a perfusate reservoir, means for pumping the perfusate, means for oxygenating the perfusate, and means for connecting the components to one another, and with the target. In a preferred embodiment the recirculating perfusion apparatus comprises a perfusate reservoir receiving efflux perfusate from the target, connected with silicone tubing passing via a peristaltic pump to a membrane lung, said membrane lung comprising about 8 m of approximately 1.47 mm inner diameter silicone tubing immersed in a circulating gas chamber filled with carboxygen gas, connected by tubing and a catheter to a target.

BRIEF DESCRIPTION OF THE DRAWINGS

FIG. 3A is at 21× magnification, FIG. 3B is at 86×, and FIG. 3C is at 214× magnification.

FIG. 4A is at 21× magnification, and FIG. 4B is at 429× magnification.

DETAILED DESCRIPTION OF THE PREFERRED EMBODIMENTS

Figure 1:
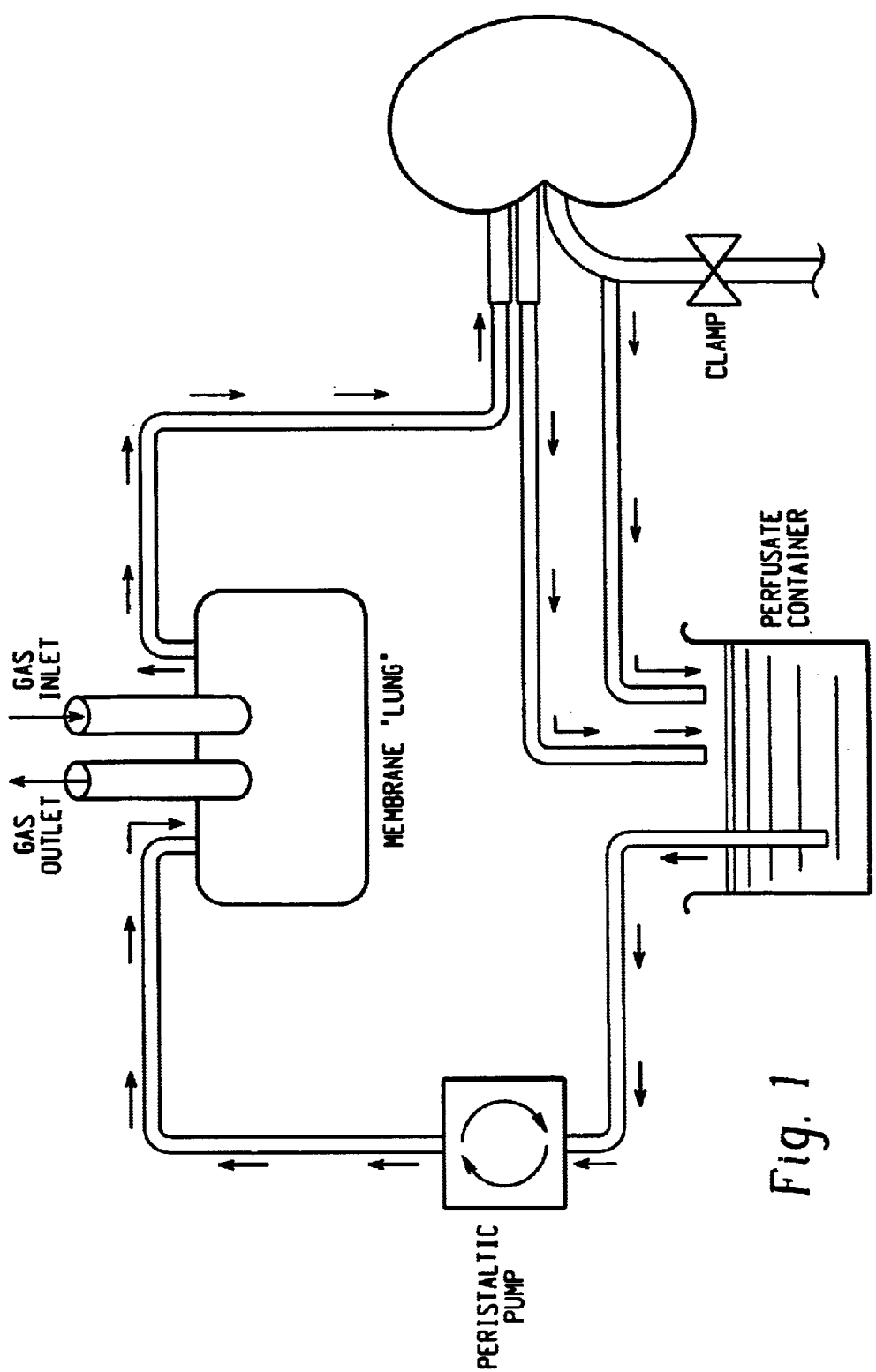
FIG. 1 is a drawing of the perfusate recirulation apparatus connected to a kidney.

As described above, the instant invention provides for methods and means for greatly enhancing the efficiency of phamaceuticals for functional use, in particular with the use of gene therapy vectors.

The following experiments illustrate surgical ex vivo and in vivo kidney perfusion using the methods and apparatus of the instant invention to effect highly efficient adenovirus-mediated gene transfer into glomerular cells, using pigs as the experimental animal. This method of gene therapy may have specific application to the treatment of kidney diseases such as Alport syndrome (Barker D et al., Identification of mutation on the COL45 collagen gene in Alport syndrome. *Science* 248:1224–1227, 1990; Tryggvason K et al., Molecular genetics of Alport syndrome. *Kidney Int.* 43:38–44, 1993; Mochizuki et al., Identification of mutations in the a3(IV) and a4(IV) collagen genes in autosomal recessive Alport syndrome. *Nature Genetics* 8:77–82, 1994).

The following examples show that gene transfer into kidney cells after intra-arterial injection was highly insignificant. Even the use of high pharmacological amounts of a number of vasodilative agents does not noticably improve the uptake of virus into the target kidney cells. In contrast, the organ perfusion system showed efficient gene transfer into glomeruli using both ex vivo and in vivo perfusion. The results of up to 80% transfer (ex vivo), or 75% transfer (in vivo), are in dramatic contrast to the results obtained with other methods of transfer into the kidney.

The perfusion system of the instant invention is applicable for gene transfer and pharmaceutical administration into a number of organs. The apparatus and methods are applicable when the target organ has a suitable blood circulation system. The flood of perfusate is most efficient if the organ has one end artery but it is not impossible to accomplish even though there are more than one. Organs which may lend themselves easily to such methods include the liver, mammary glands, spleen and lung. It is even possible to apply the instant methods to isolated segments of blood vessels. Where the pharmaceutical agent is a gene therapy vector, the construct may functionally encode for endogenous or exogenous proteins, which can then be expressed in the target after treatment. Such gene transfer will allow for the expression of various proteins by the target tissues.

The most obvious benefit of the instant perfusion system and methods is the enhanced efficiency, the target specificity for gene transfer, and the possibility of using only a small amount of vector material. Furthermore, extracorporeal perfusion systems diminish the risk of administering a large amount of foreign genetic material into the general circulation of the subject, especially important for immunocompetent individuals.

The following examples illustrate certain embodiments of the instant invention and are meant by way of illustration and not limitation.

EXAMPLE 1

Materials and Methods

Reporter gene virus construct—A replication defective recombinant adenovirus (AdCMVlacZ, Dr. James Wilson, Human Gene Therapy Institute, Wistar Institute, U. Penn.) containing the cytomegalovirus promoter and $E.$ $coli$ β-galactosidase gene as a reporter gene was used as the gene transfer vector (Engelhardt et al., supra.) The vector has been deleted of sequences in the E3, E1A and E1B regions, imparing the ability of this virus to replicate and transform non-permissive cells (Hurwitz et al., Evidence that a second tumor antigen coded by adenovirus early gene region E1a is required for efficient cell transformation. $PNAS(USA)$ 82:163–167, 1985). Adenoviral stocks of recombinant virus were prepared and purified through double CsCl banding (Engelhardt et al., supra.). Titers of viral stocks were determined by plaque assay using 293 human embryonic kidney cells (ATCC CRL1573). The viral preparations were stored in 10 mM Tris-HCl, 10% glycerol at −70 C. until use. The viral preparations were tested for replication competence by extended cultivation on HeLa cells. Expression of the reporter gene was used to identify cells where successful transduction had occurred.

Experimental animals—Experimental animals were young 22–35 kg farm pigs which were treated according to institutional guidelines. In this experiment, operative gene transfer trials were made to 16 animals. The animals were under general anesthesia during the operation. Azaperon (Stresnil) 4 mg per kg was first administered as intramuscular injection. For induction, medetomidine (Domitor) 80 μg per kg, ketamin (Ketalar) 4 mg per kg and atropine (Atropin) 0.05 mg per kg were given intramuscularly. Thiopenthal (Hypnostan) 5 mg per kg was then given intravenously, the animal was intubated, and the anesthesia was continued under a combination of nitrous oxide-oxygen (1:1) and 1.5% enflurane (Efrane).

EXAMPLE 2

Cultured Human Cells—Human endothelial cells, prepared from the iliac vein and artery of organ donors, were grown in M119 medium supplemented with 20% fetal calf serum (FCS), 100 IU/ml penicillin, 100 μg/ml streptomycin and 30 μg/ml endothelial cell growth factor (Sigma). Mesangial cells were isolated from human glomeruli and identified by light microscopy, based on their typical smooth muscle cell like morphology, and by other immunohistochemical markers (Holthöfer et al., Rat glomerular cells do not express podocytic markers when cultured in vitro. $Lab.$ $Invest.$ 65: 548–557, 1991). The mesengial cells were grown in RPMI medium supplemented with 10% FCS, 100 μg/ml penicillin and 100 μg/ml streptomycin. In addition, a supplement of insulin (25 μg/ml), transferrin (25 μg/ml) and selenium (25 ng/ml) (SIGMA) was added to the culture medium.

Isolation of human kidney glomeruli—Intact human glomeruli were prepared from renal cortex of histologically normal portions of the non-involved kidney poles of tumor nephrectomy specimens. The glomeruli were isolated by a standard three-stage sieving method (Misra R P, Isolation of glomeruli from mammalian kidneys by graded sieving. $Am.$ $J.$ $Clin.$ $Pathol.$ 58: 135–139, 1972; Tryggvason et al., Number of nephrons in normal human kidneys and kidneys of patients with the congenital nephrotic syndrome. $Nephron$ 15: 62–68, 1975), by passing renal cortex tissue sequentially through stainless steel sieves of sizes 250, 210 and 75 um. The smallest pore size retained an almost pure glomerular fraction, which was transferred to six-well plastic plates. The glomeruli were cultured in RPMI1640 medium supplemented with 100 μg/ml penicillin, 100 μg/ml streptomycin, 10% FCS, 5 μg/ml insulin, 5 μg/ml transferrin and 5 ng/ml selenium.

In vitro gene transfer into cell lines and isolated glomeruli—Cultured human endothelial or mesangial cells were infected with the recombinant virus in a medium containing 2% FCS at multiplicity of infection (MOI) of 1 or 10 per cell. Following 2 hour incubation, the medium was changed to complete culture medium and the cells were grown for an additional 72 hours and stained with X-gal to study the transfer and expression of the lacZ reporter gene.

The isolated glomeruli were infected with MOI $10^3$–$10^7$ per single glomerulus by incubating the glomeruli with the virus in the supplemented culture medium in the presence of 1% FCS. In the infection of the control sample 10 mM Tris was used. Following 6 or 16 hours of incubation, the glomeruli were rinsed with fresh medium to remove the remaining virus and cultured in complete medium containing 20% FCS. The glomeruli were stained cytochemically three days after infection by adding 1 mg/ml X-gal into the culture medium. Blue β-galactosidase staining was usually visible after a 2 hour incubation at 37 C.

Results

Adenoviral gene transfer into cultured cells and isolated glomeruli—Primary cultures of human endothelial and mesangial cells that were exposed for two hours to recombinant virus exhibited strong staining for the expression of the lacZ reporter gene (data not shown). Exposure of the cells to virus at an MOI of 100 for 24 hours resulted in expression of the reporter gene in the majority of the cells with no apparent changes in cell morphology. Expression of the lacZ gene appeared about 8 hours following addition of the virus.

The isolated human glomeruli, some of which had lost the Bowman's capsule, could be maintained viable in culture for several days without losing their morphology. During this period, virus infection was carried out and gene transfer efficiency measured. At an MOI of about 1000 virus per glomerulus, expression of the lacZ gene was observed in practically all glomeruli, with all cell types showing positive staining reactions (FIG. 2).

Figure 2:
FIG. 2 shows the expression of β-galactosidase in porcine kidney following ex vivo perfusion with AdCMVlacZ virus.

FIG. 2 shows cryosections of the explanted kidney samples stained with X-gal and HE. The sections show expression of the β-galactosidase in isolated human glomeruli infected with AdCMVlacZ virus. The glomeruli were infected with the virus for about 6 hours, incubated without virus for 12 hours and then stained with X-gal. Most of the glomeruli exhibited intense expression which appeared to involve all cell types of the glomerulus.

EXAMPLE 3

Animals and Histological Staining—as describe in Example 1.

Intra-arterial Infusion—The virus vector was injected into the renal artery during laparotomy during these tests. Eleven animals were operated. In the first experiment 2.5 ml ($2\times10^9$ pfu) of adenoviral preparation was injected through a 0.1 mm butterfly needle directly into the anterior branch of the left renal artery. The animal was sacrificed on the third postoperative day and nephrectomy was made. Kidney samples were taken for histologic examination and expression of the lacZ gene was examined following staining with X-gal. Because the infusion was made to the lower pole of the kidney, the upper pole was used as control. Nine of the eleven animals were operated according to a similar scheme as above, except that the vasodilative pharmacological agents were infused intra-aterially into the anterior branch of the renal artery shortly prior to infusion of the virus preparation in an attempt to diminish the potential vascular resistance in the kidney. Five vasodilative agents were used in different trials; papaverin, alprostadil, enalapiril, verapamil and lidocain. One animal was treated as a control by infusing 10 ml of saline into the renal artery before the viral infusion. The amount of virus injected in these trials was $4\times10^9$ pfu in 8 ml 0.9% saline.

Histochemical analysis—Efficiency of adenoviral gene transfer was monitored by analysis of lacZ gene expression on cryosections. Sections of 5 μm thickness were first fixed for 10 minutes in 4% gluteraldehyde in PBS. Following extensive washings with 1xPBS, the sections were incubated in a detergent solution containing 0.01% sodium deoxycholate, 0.02% NP40 and 2 mM magnesium chloride in PBS for 10 minutes. The sections were incubated in an X-gal solution (detergent solution containing 5 mM potassium ferricyanide, 5 mM potassium ferrocyanide and 1 mg/ml X-gal (5-bromo-4-chloro-3indolyl β-galactopyranoside) for 3 hours overnight at 37 C., and subsequently counterstained with PAS. Possible cytotoxic effects of the virus were evaluated by histological examination of formaldehyde-fixed paraffin embedded tissue sections after PAS-hematoxylin staining.

Results

Gene transfer by infusion into kidney in vivo—These experiments did not lead to successful gene transfer into kidney cells. LacZ gene expression was observed in only a few scattered cells in the kidney cortex, no signs of expression were seen in the glomeruli (data not shown). Use of vasodilative agents immediately prior to injection of the virus had no visible effect on the efficiency of gene transfer. Even use of several, up to three consecutive injections at 2 minute intervals, did not markedly increase the efficiency of gene transfer (data not shown).

EXAMPLE 4

Animals and Histological Staining—as described in Example 1.

Kidney perfusion system—In order to extend the time available for infection of target kidney cells by the virus vector, an apparatus was developed which provided a closed-circuit perfusion system for the continuous circulation of the virus solution in the intact kidney in vivo and ex vivo. This system, as shown in FIG. 1, consists of a reservoir for the perfusate, a pump, an artificial membrane lung, connected to the kidney to be perfused, all connected by 3 mm inside diameter silicon tubing. The reservoir for the experiment was a 300 ml glass bottle container placed in a 37 C. water bath. The peristaltic pump was from a portable organ fixation perfusion machine (PF-3A; Gambro) with a flow rate (rpm) control. The membrane lung consists of 8 m of 1.47 mm inside diameter silicon tubing in a 2000 ml glass container gassed with carbogen (95% oxygen, 5% carbon dioxide) at a pressure of 15 mm Hg, according to Hamilton et al., (Inexpensive membrane lung for small organ perfusion. *J. Libid. Res.* 15:182–186, 1974). The kidney was attached to the perfusion system by cannulating the renal artery with 14 G cannula and the renal vein with a 12 G cannula. The venous and ureter effluents were collected directly into the reservoir. The perfusate had a total volume of 350 ml and contained previously separated red blood cells at a hemocrit value of 17% in Krebs-Ringer solution. Additionally, 25,000 IU heparin, and antibiotics were added. For ex vivo perfusion of explanted kidneys, the perfusate also contained 20,000 IU penicillin, 20,000 μg streptomycin as antibiotics and 5 ml MEM amino acid solution. For the in vivo perfusions, the perfusate contained 250 mg cefuroxim as antibiotic. There was no direct measurement of perfusion pressure in the kidney. To circumvent this problem, the flow rate was adjusted to enable adequate diuresis. The pH and oxygen saturation in the perfusate was measured using routine laboratory "blood gas" analysis of the perfusate.

Kidney perfusion ex vivo—Before connecting the kidney to the perfusion system, a 10 ml lidocain-heparin solution (190 mg lidocain+5,000 IU heparin) and 0.9% saline were infused through the renal artery until the venous effluent was clear. The adenovirus preparation ($1\times10^{11}$ pfu in 20 ml Krebs-Ringer solution) was then infused into the arterial inlet, and the perfusion was immediately initiated. The flow rate was set at 100–200 ml/min. Diuresis and extraction of virus into the urine were measured throughout the perfusion period.

A total of four kidneys were perfused ex vivo, the average perfusion time being 12 hours. Following the experiments, tissue samples were taken for histologic analysis as described above.

Kidney perfusion in vivo (in situ)—Kidneys of three animals were perfused in vivo via laparotomy. The animals were given prophylactic antibiotic (750 mg cefuroxim) intravenously prior to the operation, 250 mg cefuroxim being added to the perfusate. While the kidney was connected to the perfusion system, it was isolated from the systemic circulation by clamping the renal artery and vein proximally. The ureter was also clamped and ureterostomy was made to collect the effluent into the perfusate and to monitor diruesis. Since perfusion pressure in the kidney could not be measured directly, the flow was kept constantly at 100–120 ml per minute. The diuresis was considered an indicator of sufficient perfusion pressure. The in vivo perfusions were carried out for 60 or 120 minutes. Hydrocortisone 50 mg was administered intramuscularly after the operation. Two animals were sacrificed on the fourth postoperative day and the kidney was removed for histologic examination. One animal was maintained for up to three weeks postoperatviely, renal biopsies being taken on days 14 and 21 after which the animal was sacrificed.

Results

Figure 3:
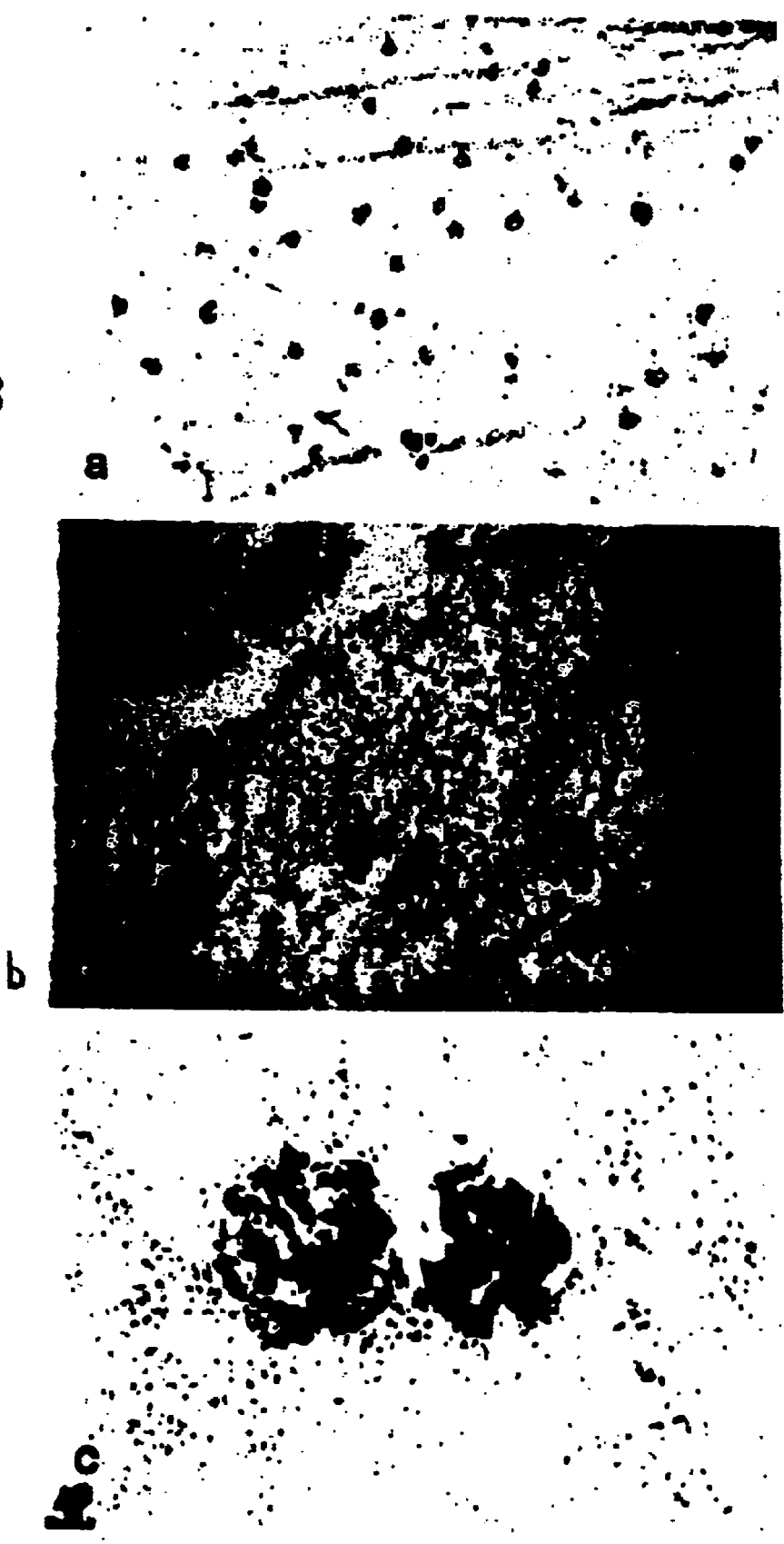
FIG. 3 shows the expression of β-galactosidase in porcine kidney following in vivo perfusion with AdCMVlacZ virus.

Gene transfer by kidney perfusion ex vivo—Perfusion of explanted kidneys with adenovirus at room temperature for up to 17 hours did not result in effective gene transfer to kidney cells (data not shown). In contrast, when perfusion was carried out at 37 C. for 12 hours, marked gene transfer could be seen in glomerular cells. By histologic examination, lacZ gene expression was observed in approximately 80% of the glomeruli, and in several glomeruli most mesangial and endothelial cells as well as epithileal podocytes appeared to be positive (FIG. 3). However, only little staining was seen in endothelial cells of blood vessels elsewhere in the kidney, and epithelial cells of the tubuli did not exhibit any staining.

FIG. 3 shows the expression of $\beta$-galactosidase in porcine kidney following ex vivo perfusion with AcCMVlacZ virus. FIG. 3(A) shows the intense expression of staining in a large proportion of the glomeruli, while little if any staining was seen in other regions of the kidney (Magnification is 21×). FIG. 3(B) shows staining for $\beta$-galactosidase in mesangial, endothelial and epithelial cells of the glomeruli, while the cells of the Bowman's capsule are negative (Magnification is 86×). FIG. 3(C) shows the expression of $\beta$-galactosidase in two individual glomeruli. (Magnification 214×).

Figure 4:
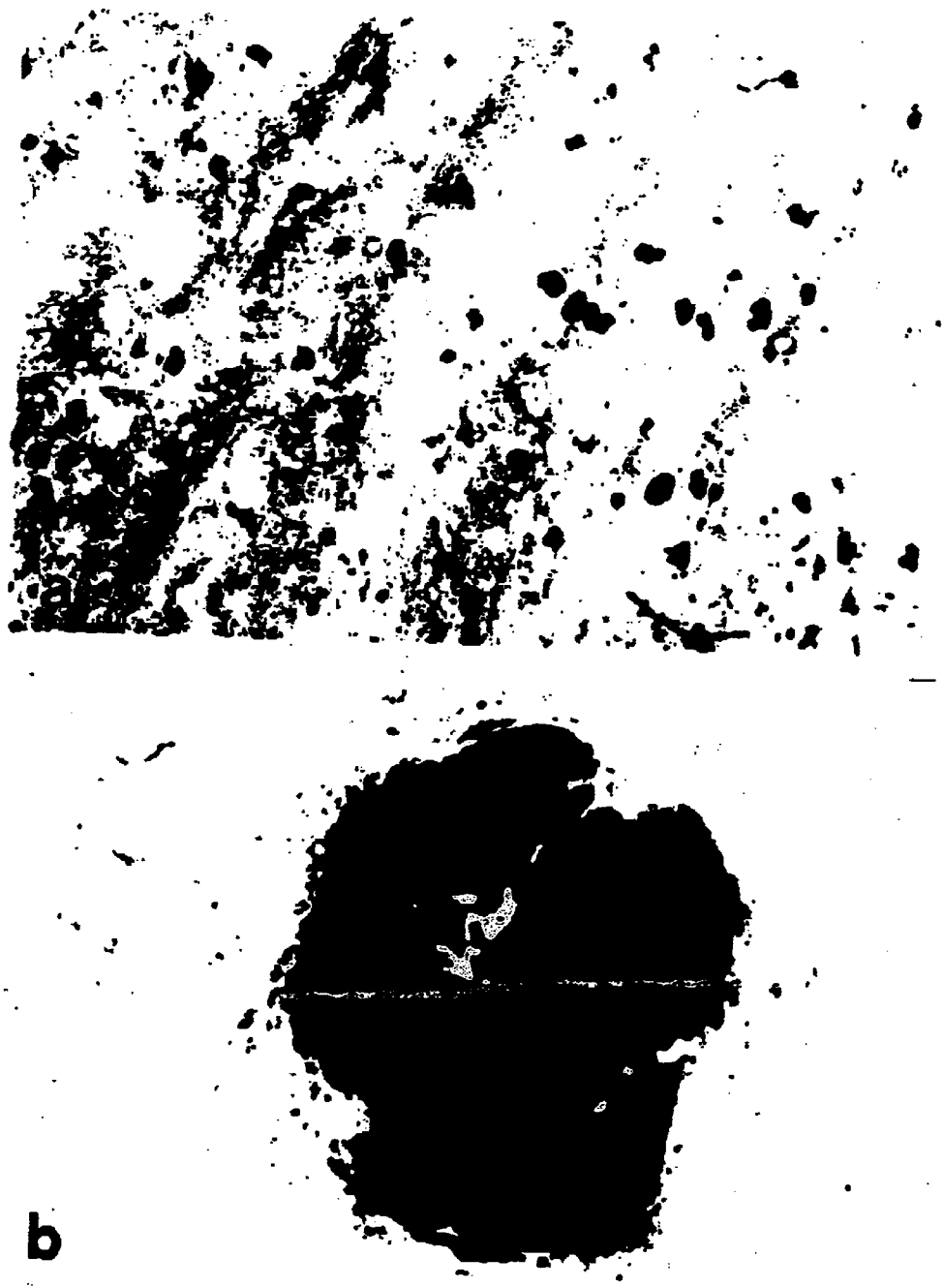
FIG. 4 shows the expression of β-galactosidase in isolated human glomeruli infected with AdCMVlacZ virus.

Gene transfer into kidney by perfusion in vivo—The first in vivo perfusion was carried out for 60 minutes, diuresis being normal during that period. Four days postoperatively lacZ gene expression was seen practically only in glomerular cells (FIG. 4). Expression was found in 9 to 45% of the glomeruli, the mean value being 27% as determined from cross-sections from experimental animals. Within the glomeruli themselves between 2 and 50% of the cells were estimated to exhibit expression. Expression was not observed in cells of other segments of the kidney, except for some vascular endothelial cells.

The other in situ perfusions were performed for 120 minutes. There was marked polyuria, the diuresis being about 800 ml during the first hour and 1200 ml during the second hour. Four days later lacZ gene expression was observed in 23 to 75% of the glomeruli, the mean being 58% depending upon the section. In individual glomeruli expression was seen in most mesangial and endothelial cells as well as in the epithelial podocytes. In certain segments all glomeruli appeared to be positive with seemingly all cells exhibiting expression (FIG. 4). In this experiment expression was only seen in scattered endothelial cells elsewhere in the vascular system and epithelial cells of proximal and distal tubuli were negative.

FIG. 4 shows expression of $\beta$-galactosidase in porcine kidney following in vivo perfusion with AdCMVlacZ virus. The kidney was perfused in situ with a closed-circuit oxygenated system at 37 C. for 2 hours. A kidney biopsy was taken 5 days later and cryosections were stained with X-gal and PAZ. FIG. 4(A) shows intense expression in a large proportion of the glomeruli, while little if any staining was seen in other sections of the kidney. (Magnification 21×). FIG. 4(B) shows the staining for $\beta$-galactosidase in mesangial, endothelial, and epithelial cells of a single glomerulus, while cells of the Bowman's capsule are negative. (Magnification 429×).

While the invention has been described with respect to certain specific embodiments, it will be appreciated that many modifications and changes may be made by those skilled in the art without departing from the spirit of the invention. It is intended, therefore, by the appended claims to cover all such modification and changes as fall within the true spirit and scope of the invention.

We claim:

1. A perfusion system for the delivery of pharmaceuticals in a perfusate to target tissues, said system comprising a perfusate solution containing gene therapy pharmaceuticals wherein said perfusate solution is maintained at a temperature of about 37° C., a means for allowing the conduction of perfusate, a reservoir for the perfusate, a means for propelling the perfusate, a means for oxygenating the perfusate, and suitable means for connecting the apparatus to a target tissue wherein the reservoir, means for propelling the perfusate, means for oxygenating the perfusate and target tissue are serially connected by a means to allow the conduction of perfusate.

* * * * *